US00PP26465P3

(12) United States Plant Patent
Schoone

(10) Patent No.: US PP26,465 P3
(45) Date of Patent: Mar. 8, 2016

(54) ***PHALAENOPSIS* ORCHID PLANT NAMED 'AVA STAR'**

(50) Latin Name: *Phalaenopsis hybrida*
Varietal Denomination: Ava Star

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 171 days.

(21) Appl. No.: 13/998,016

(22) Filed: Sep. 24, 2013

(65) Prior Publication Data

US 2014/0090131 P1 Mar. 27, 2014

Related U.S. Application Data

(60) Provisional application No. 61/705,229, filed on Sep. 25, 2012.

(30) Foreign Application Priority Data

Sep. 27, 2012 (NL) ..... PBR OPS971

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

(56) References Cited

U.S. PATENT DOCUMENTS

PP10,681 P * 11/1998 Plate ..... Plt./311

* cited by examiner

*Primary Examiner* — June Hwu
(74) *Attorney, Agent, or Firm* — Foley & Lardner LLP; Sunit Talapatra

(57) ABSTRACT

A new and distinct *Phalaenopsis* plant named 'Ava Star' particularly characterized by flowers which are white with a red/purple labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Ava Star'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Ava Star'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Ava Star' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Ava Star' originated from a cross made by the inventor in 2000 in Strengweg, Heemskerk, The Netherlands. The female or seed parent is the *Phalaenopsis* cultivar designated 'Percy Porter', unpatented. The male or pollen parent is the *Phalaenopsis* cultivar designated 'Red Eye', unpatented. The new *Phalaenopsis* 'Ava Star' was discovered and selected by the inventor as a single flowering plant within the progeny of the stated cross in a controlled environment in 2008 in Strengweg, Heemskerk, The Netherlands.

Asexual reproduction of the new *Phalaenopsis* cultivar by tissue culture (mericloning) was first performed in July, 2008 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Ava Star', which in combination distinguish this *Phalaenopsis* as a new and distinct cultivar:

1. flowers which are white with a red/purple labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Ava Star', the female parent 'Percy Porter' has white flowers and they are about 12 cm in size. The male parent 'Red Eye' has white colored flowers with a purple labellum and they are about 9 cm in size, whereas the flowers of 'Ava Star' are white with a red/purple labellum and are about 10.5 cm in size.

Presently, the commercial cultivar to which 'Ava Star' can be meaningfully compared is 'Balysa' (Patented, U.S. Plant Pat. No. 10,681). They both are white with a contrasting red/purple labellum. However, Balysa has smaller flowers than 'Ava Star' and also the size of the plant of 'Balysa' is smaller than 'Ava Star'.

BRIEF DESCRIPTION OF THE PHOTOGRAPHS

The accompanying photographs illustrate the overall appearance of the new *Phalaenopsis* 'Ava Star' showing the colors as true as is reasonably possible with colored reproductions of this type. Colors in the photographs may differ slightly from the color values cited in the detailed botanical description, which accurately describe the color of 'Ava Star'.

DETAILED BOTANICAL DESCRIPTION

Figure 1:
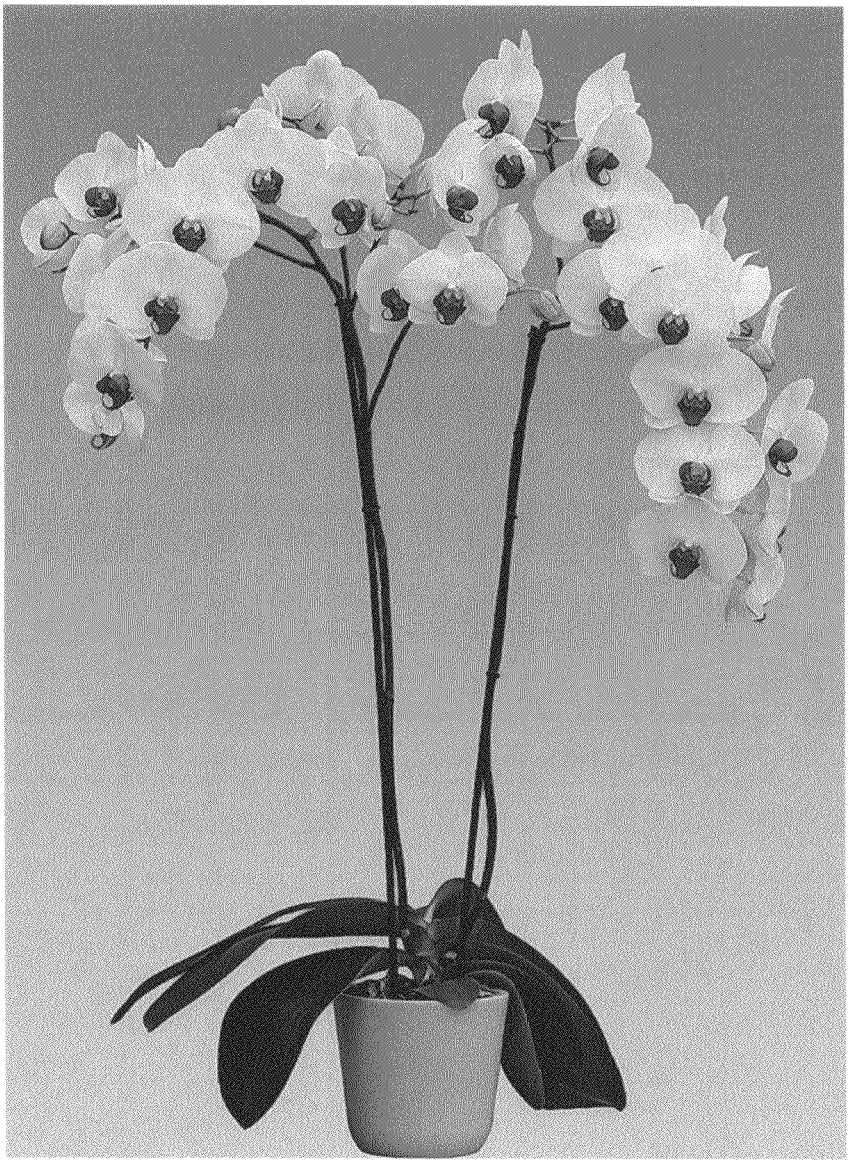
FIG. 1 shows a side view perspective of a typical flowering plant of 'Ava Star' in a 12 cm pot, at 16 months of age.

The new *Phalaenopsis* cultivar 'Ava Star' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Ava Star' as grown in a greenhouse in Strengweg, Heemskerk, The Netherlands, under conditions which closely approximate those generally used in commercial practice. Initially, the ideal temperature to grow plants of 'Ava Star' is 27° C. during the day and at night. Then, during the flowering phase of 'Ava Star', the ideal growing temperature is 20-22° C. during the day and 18° C. at night. Light levels for growing 'Ava Star' are a minimum of 5,000 lux and a maximum of 10,000 lux. A balanced fertilizer with level of 200 ppm N, 87 ppm P, 168 ppm K is applied. Duration of growth of 'Ava Star' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Ava Star' plants described is 12 months after potting.

Classification:

*Botanical.*—*Phalaenopsis hybrida.*

Parentage:

*Female or seed parent.*—*Phalaenopsis* cultivar designated 'Percy Porter', unpatented.

*Male or pollen parent.*—*Phalaenopsis* cultivar designated 'Red Eye', unpatented.

Propagation:

*Type.*—Tissue culture (mericloning).

*Rooting habit and description.*—Approximately 4 mm-6 mm wide and grey/green (RHS 193C) in color; freely branching. It takes 12 weeks for plants growing in tissue culture to initiate roots.

Plant:

*Size at maturity.*—Height (from bottom of pot to highest flower): about 70 cm to 90 cm. Spread: about 50 to 70 cm.

*Growth habit.*—Large; green (RHS 143B) leaves and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1-2 racemes with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, the tip is little pointy and asymmetric.

*Texture (both surfaces).*—Smooth and leathery.

*Pubescence.*—None.

*Mature leaf length.*—About 15 to 30 cm.

*Mature leaf width.*—About 6 to 10 cm.

*Mature leaf thickness.*—About 2 mm.

*Mature leaf color.*—Upper side: RHS 141B. Under side: RHS 143B.

*Leaf base.*—Acute.

*Margin.*—Entire.

*Venation.*—Pattern: parallel. Color of midvein: upper side: green (RHS 141B). Under side: green (RHS 143B).

Inflorescence description:

*Appearance.*—Upright to slightly pendant, racemose inflorescence with bilaterally symmetrical flowers that open in succession beginning with the lowermost flower.

Raceme:

*Quantity per plant.*—About 1 to 2.

*Number of flowers per raceme.*—About 10 to 25.

*Length.*—About 85 cm.

*Peduncle.*—Diameter: about 6 mm. Strength: strong. Aspect: upright. Texture: glabrous and smooth. Color: combination of RHS 146D & RHS N200A.

*Buds.*—Height (from base to tip): about 30 mm. Diameter (at midpoint): about 24 mm. Shape: oval/egg-shaped. Color: RHS 154C.

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 1-2 racemes appear with flower buds and flowers. First flowers can be expected approximately 4 to 6 months after planting a plant with a leaf diameter of 3 to 5 cm. Flowers persistent.

*Flowering longevity.*—On the plant: about 4 to 6 months; lastingness of cut flowers: has not been observed.

*Fragrance.*—No fragrance.

Figure 2:
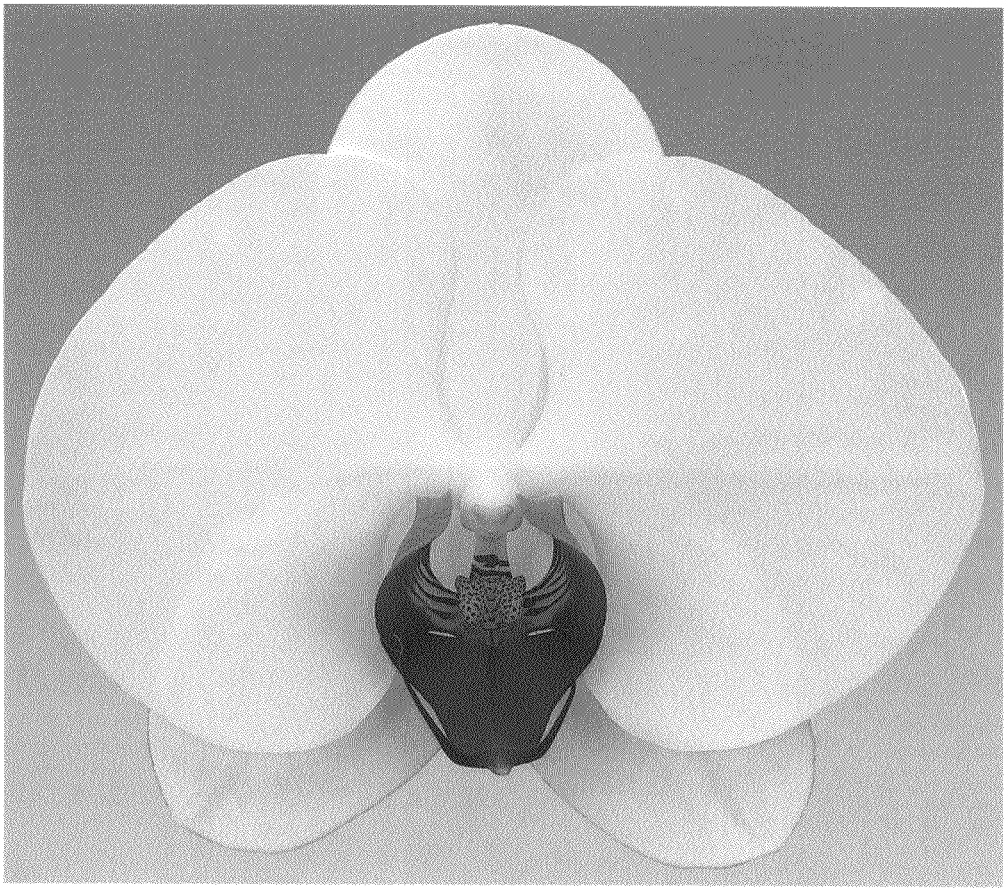
FIG. 2 shows a close-up view of a typical flower of 'Ava Star'.
Figure 3:
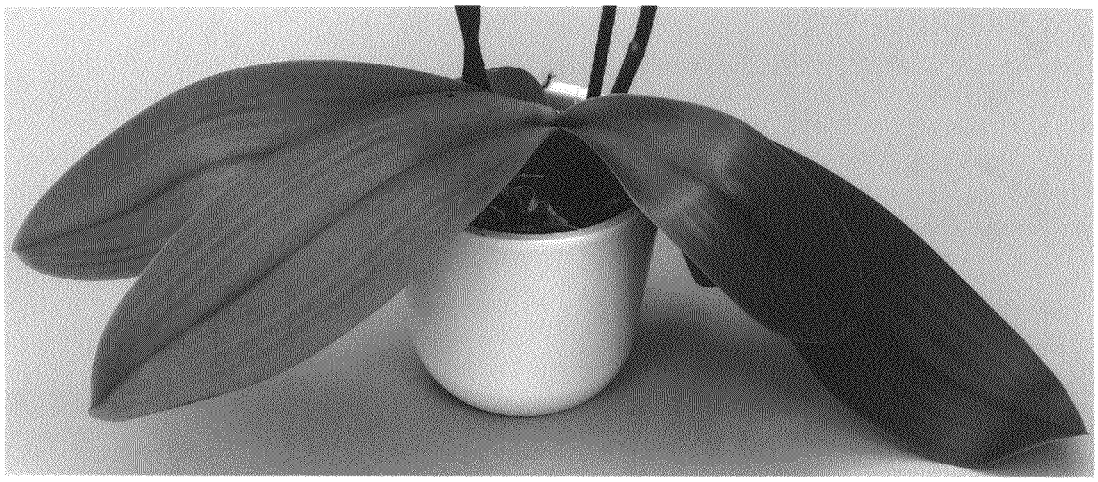
FIG. 3 shows a close-up view of the typical leaves of 'Ava Star'.

*Flower.*—Rate of opening: Flowers fully opened about 2 to 3 days after petal and sepal separation. Orientation at opening: slanted upward and outward. Shape: Typical shape of *Phalaenopsis* orchid, see FIG. 2. Size (of single bloom): Height: about 80-100 mm. Diameter: about 90-110 mm. Quantity and arrangement: Three petals and three sepals that are trimerous and arranged in 2 overlapping whorls. Inner whorl of 3 petals is comprised of 2 lateral petals and a labellum. Petals are more pronounced than sepals.

*Petals.*—2 lateral petals: Overall shape: broadly ovate and weakly cupped. Apex: round. Margin: entire and weakly undulate. Base: broadly ovate. Length: about 57 mm. Width: about 43 mm. Texture: Upper surface: smooth and satiny. Under surface: smooth and satiny. Color (when fully opened): upper and under surface: white (RHS NN155C). Labellum: Overall shape: 3-lobed with 2 prominent callosities at central junction of the lateral lobes and base of the midlobe. Lateral lobes of labellum fold upward about the column; the midlobe extends forward and is terminated by 2 long filiform appendages at the apex. Lateral lobes of the labellum are ovate in shape while the midlobe is triangular with a bump and a rib on it. Margin: entire and weakly undulate. Apex of the midlobe and lateral lobes: oval. Length midlobe: about 21 mm. Width (not flattened) midlobe: about 25 mm. Length lateral lobe (not flattened): about 17 mm. Width (not flattened) lateral lobes: about 19 mm. Depth of tube created by lateral lobes of labellum: about 19 mm. Texture: Upper & under surface: smooth and satiny. Color (when fully opened): Midlobe, upper surface: red/purple (RHS 72A). The edge at the base is greyed/red (RHS 179B). Under surface: In the center, from base all the way down to the end, there is white (RHS NN155D), next to that on the sides red/purple (RHS 70B). The outer edge is red/purple (RHS 72A). Upper edge at the base is greyed/purple (RHS 183C) and some yellow/orange (RHS 23C). Lateral lobes, upper surface: At the base white (RHS NN155D) with greyed/purple stripes (RHS 183A) which runs into RHS 71A. At the bottom first RHS 59A, which runs into the main color red/purple (RHS 72B). Under surface: At the base white (RHS NN155D) with purple stripes (RHS N78A). At the bottom red/purple (RHS 59A) which runs into the main color RHS N78C. At the upper edge also a little RHS 23C. Chirri: long with large curl at the end (about 25 mm). Color: red/purple (RHS 59A) and tip is white (RHS NN155B). Pestle (Callosities): Length: about 5 mm. Width (not flattened): about 7 mm. Pubescence: none. Color: main color is yellow (RHS 13B). There is also with some white on the Pestle (RHS NN155C) and some red/purple spots (RHS 59A).

*Sepals.*—Arrangement: 3 sepals, one dorsal and two laterals. Overall shape: elliptical and weakly cupped. Margin: entire and weakly undulate. Length: about 46 mm. Width: about 34 mm. Apex: oval and little pointy. Texture: Upper & under surface: smooth and satiny. Color (when fully opened): Dorsal, upper surface: white (RHS NN155C). Under surface: white (RHS NN155D) with a red/purple haze (RHS 72B). Lateral, upper surface: white (RHS NN155C) with a yellow/green haze (RHS 145C. At the base some stripes/spots RHS N78A. Under surface: white (RHS NN155D) with a yellow/green haze (RHS 145C). The midvein is purple (RHS N78A). The edges also have a haze of RHS N78A.

*Pedicel.*—Length: about 40 mm. Diameter: about 3 mm. Texture: glabrous and smooth. Color: Close to the flower white (RHS NN155C), which runs into yellow/green (RHS 145D).

Reproductive organs:

*Arrangement.*—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed or fruit.

*Column.*—Length: about 8 mm. Diameter: about 5 mm. Color: white (RHS NN155B).

*Pollinia.*—Quantity: Two. Diameter: about 1.5 mm. Color: yellow/orange RHS 14B.

*Ovary.*—Length: about 4 mm. Diameter: about 3 mm. Color: RHS NN155C.

Pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Ava Star', as illustrated and described herein.

* * * * *